United States Patent
O'Lenick, Jr. et al.

(10) Patent No.: US 7,195,786 B1
(45) Date of Patent: Mar. 27, 2007

(54) CRANBERRY AMIDO AMINES AND BETAINES AS A DELIVERY SYSTEM FOR NATURAL ANTIOXIDANTS

(75) Inventors: Anthony J. O'Lenick, Jr., Dacula, GA (US); Carter LaVay, Riverside, CT (US)

(73) Assignee: Zenitech LLC, Old Greenwich, CT (US)

( * ) Notice: Subject to any disclaimer, the term of this patent is extended or adjusted under 35 U.S.C. 154(b) by 548 days.

(21) Appl. No.: 10/600,251

(22) Filed: Jun. 23, 2003

(51) Int. Cl.
*A01N 65/00* (2006.01)
(52) U.S. Cl. .................................... 424/725
(58) Field of Classification Search .................. None
See application file for complete search history.

(56) References Cited

U.S. PATENT DOCUMENTS 6,391,345 B1    5/2002    Heeg et al.

*Primary Examiner*—Michael Meller

(57) ABSTRACT

The present invention relates to Cranberry seed oil derivatives derived by the reaction of dimethyl amino propyl amine and cold pressed Cranberry seed oil. This intermediate is subsequently reacted with sodium monochloroacetic acid to make a Cranberry betaine. The choice of cold pressed Cranberry seed oil as a raw material in the preparation of the compounds of the present invention is critical, since it has been found that the cold pressed Cranberry seed oil contains antioxidants, antimicrobial compounds and which when reacted with a DMAPA result in products that deliver said actives to the skin and hair, resulting in protection of the skin and hair from environmental factors such as acid rain, ozone attack and UV degradation.

2 Claims, No Drawings

CRANBERRY AMIDO AMINES AND BETAINES AS A DELIVERY SYSTEM FOR NATURAL ANTIOXIDANTS

BACKGROUND OF THE INVENTION

The present invention relates to Cranberry seed oil derivatives derived by the reaction of dimethyl amino propyl amine, and cold pressed Cranberry seed oil. The choice of cold pressed Cranberry seed oil as a raw material in the preparation of the compounds of the present invention is critical, since it has been found that the cold pressed Cranberry seed oil contains a unique antioxidant which when reacted with a dimethyl amino propyl amine result in products that deliver said actives to the skin and hair, resulting in protection of the skin and hair from environmental factors such as acid rain, ozone attack and UV degradation.

U.S. Pat. No. 6,391,345 issued May 2002 describes the refining of cold pressed cranberry seed oil, and is incorporated herein by reference. American cranberries, *Vaccinium macrocarpon*, are native plants of open, acid peat bogs in North America. Cranberry plants are evergreen perennial vines that produce runners and upright branches with terminal flower buds.

Cranberries have historically been harvested and either ingested as whole berries, such as in cranberry sauce, or have been processed for their juice. Pulp remaining after cranberry juice extraction processing has historically been regarded as an undesirable waste product with little or no utility.

In the United States, cranberries are grown and are harvested in the Northeast, Northwest and Great Lakes regions. Cranberries ripen and are harvested in autumn, which has made cranberries a holiday food. Cranberries have not changed significantly in appearance and nutritional value over time. Cranberries have typically been stored by freezing or drying the whole berries.

Cranberries have become a popular food only in recent years because cranberries have a very bitter taste. Historically, processors have not dealt well with the taste. Cranberries are known to contain quininic acid. It is the quininic acid that imparts to cranberries, the bitter taste. Cranberry juice has become more palatable because it is blended with other sugar-containing aqueous liquids.

Apart from an undesirable taste, quininic acid is believed to have nutraceutical properties. When ingested, quininic acid is converted to hippuric acid. Hippuric acid is believed to remove toxins from the bladder, kidneys, prostate and testicles. Under normal circumstances, oils useful in the cosmetic industry are refined with a variety of steps that are designed to maximize triglyceride content, and minimize color and odor. These steps include steam distillation, a process in which steam is sparged through the oil to remove odor and color bodies and solvent extraction with compounds like hexane, which remove additional odor and color bodies. We have learned that these processes, while improving color and odor, remove many of the desirable "active" materials like tocopherols, antioxidants and the like. What results is a light color, low odor triglyceride with no appreciable added skin benefits. We have surprisingly learned that when the cranberry seed oil that is cold processed is reacted with specific compounds, the actives (normally removed in non-cold press process) remain in the product, become water-soluble and have outstanding activity on the skin. In essence two things happen when the cold pressed cranberry seed oil is reacted with dimethylaminopropyl amine. First the triglyceride reacts with the amino group of the DMAPA, giving a product which when neutralized to pH 7 in water is water-soluble. Secondly, the water-soluble product solubilized the active components there as a consequence of cold pressing. Thirdly, these very desirable materials are deposited on the skin and have a proclivity to remain on the skin. The result is a unique delivery of the actives to the skin from totally natural fruit oil.

The compounds of the present invention all get their properties from a common intermediate, an amido amine. This amido amine is transformed into betaines, quats and amine oxides with unique properties in personal care applications.

SUMMARY OF THE INVENTION

The present invention relates to a series of products derived from the reaction of cold pressed Cranberry oil and dimethyl aminopropyl amine. The derivatives include betaines, amine oxides and quaternary compounds. The dimethyl aminopropyl amine intermediate is a key product in the preparation of the other compounds, and is key to the functionality.

The present invention also relates to a process of treating hair and skin, which comprises contacting the hair and skin with an effective anti-oxidant containing amount of Cranberry compounds of the preset invention.

DETAILED DESCRIPTION OF THE INVENTION

U.S. Pat. No. 6,391,345 issued May 2002 describes a cold pressed process for cranberry oil. We have surprisingly found that if the same process is used on Cranberry oil specific antioxidant materials that are removed by more aggressive refining processes like solvent extraction. These compounds surprisingly survive the reaction with DMAPA resulting in a highly substantive delivery system for these very desirable natural compounds.

Also critical to the practice of the present invention is the fatty composition of the cold pressed Cranberry oil. This Cranberry oil has a substantially clear appearance with a pale yellow color.

Cold Pressed Cranberry Oil is a triglyceride conforming to the following structure:

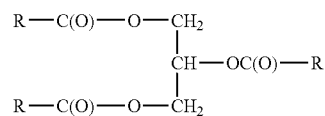

The R—C(O)— group has the following composition:

| Component | % Weight |
|---|---|
| 16:0 palmitic | 5.0 to 6.0 |
| 18:0 stearic | 1.0 to 2.0 |
| 18:1 oleic | 20 to 25 |
| 18:2 linoleic | 35 to 40 |
| 18:3 linolenic (alpha) | 30 to 35 |
| 20:0 arachidic | 0.13 |
| 20:1 gadoleic | 0.20 |
| 20:5 (n-3) | 0.32 |
| 22:2 | 1.1 |
| Myristic | 0.01 |

-continued

| Component | % Weight |
|---|---|
| Pentadecanoic | 0.02 |
| Palmitoleic (trans) | 0.13 |
| Palmitoleic (cis) | 0.08 |
| 10-heptadecanoic | 0.03 |
| Gamma linolenic | 0.1 to 0.2 |
| Nonadecanoic | 0.1 to 0.2 |
| 11-transeicosenic | 0.22 |
| 11, 14 eicosandienoic | 0.1 |
| 11, 14, 17 eicosatrienoic | 0.01 |
| Eicosapentaenoic | 0.01 |
| Behenic | 0.03 |
| Erucic | 0.02 |
| Docosapentaenoic | 0.01 |
| Tricosanoic | 0.01 |
| Lignoceric | 0.02 |
| Nervonic | 0.02 |

The oil also contains the following very critical "active" components for skin and hair care:

| Compound | mg/kg |
|---|---|
| Campesterol/brassicasterol (mg/kg) | 66.0 |
| Stigmasterol (mg/kg) | 68.0 |
| Beta-sitosterol (mg/kg) | 1319.0 |
| Phosphatidylinositiol (mg/kg) | 9.9 |
| Phosphatidylcholine (mg/kg) | 202.0 |
| Alpha-tocopherol (mg/kg) | 341.0 |
| Gamma-tocopherol (mg/kg) | 110.0 |

When the oil is exposed to steam strip and solvent extraction the concentration of the "active" components drops to vanishingly small levels and the activity is lost.

As can be seen, the cold pressed cranberry seed oil is a rich source of compounds having important properties when applied to hair and skin. Stigmasterol is an anti-stiffness factor. Beta-sitosterol has use as an antihyperlipoproteinemic agent. One or more of the campesterol, stigmasterol and beta-sitosterol has inflammatory activity and may be useful in the treatment of gingivitis, rash, eczema, and other skin lesions. It is also believed that these compounds found in cranberry seed oil have activity as sunscreen agents. Since some of the compounds present in cranberry oil have absorbance in the UV-B range. It is this range that causes the greatest cellular damage. The cold pressed cranberry oil can shield against UV-A induced damage by scattering light as well as by light spectrum absorption. The cold pressed cranberry oil has, then activity as a broad spectrum UV protectant. The cranberry oil may be used alone or in combination with other conventional sunscreens.

The phosphatidylinositiol and phosphatidylcholine and tocopherols are highly desirable materials used on skin. The phosphatidylcholine, also known as lecithin, is found in human beings in the nervous system and the brain. Lecithin also has use as an edible and digestible surfactant. It is usable in manufacturing foods such as margarine and chocolate. Lecithin is a natural antioxidant that can increase oil stability and shelf life. Lecithin also has use in pharmaceuticals, cosmetics, skin care, and in treating leather and textiles.

Cold pressed cranberry seed oil has a very high concentration of gamma tocopherol. This level is much higher than is found in oils such as safflower and grape, which are 11 and 33, respectively. The gamma tocopherol has the most antioxidant capacity of all of the tocopherols and contributes to the stability of highly unsaturated oils in the cranberry oil. It is believed that the presence of the high gamma tocopherol concentration makes cranberry oil an excellent additive to animal food—both human and non-human. The gamma tocopherol may be as important as alpha tocopherol in preventing degenerative diseases.

Cold pressed cranberry seed oil has a high linolenic acid content. Linolenic acid has been implicated as a food additive and nutraceutical in preventing coronary heart disease and cancer. Cranberry oil also has a high polyunsaturated: saturated ratio in a neutral lipid fraction, of 10:1. This ratio is regarded as having value in reducing serum cholesterol, atherosclerosis and in preventing heart disease.

Cold pressed cranberry seed oil has a rather dark yellow to orange color because it contains carotenoids. The carotenoids are usable as colorant substitutes for materials such as carotenes, annotos, and apocarotenals used in the nutraceutical and oil industries.

The cold pressed Cranberry seed oil, containing all of the above desirable compounds, is reacted with a dimethyl amino propyl amine conforming to the following structure:

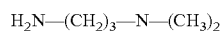

To provide an amid conforming to the following structure:

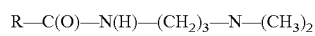

R is derived from cold pressed cranberry seed oil and has the following composition

| Component | % by Weight of "R" |
|---|---|
| 16:0 palmitic | 5.0 to 6.0 |
| 18:0 stearic | 1.0 to 2.0 |
| 18:1 oleic | 20 to 25 |
| 18:2 linoleic | 35 to 40 |
| 18:3 linolenic (alpha) | 30 to 35 |
| 20:0 arachidic | 0.13 |
| 20:1 gadoleic | 0.20 |
| 20:5 (n-3) | 0.32 |
| 22:2 | 1.1 |
| Myristic | 0.01 |
| Pentadecanoic | 0.02 |
| Palmitoleic (trans) | 0.13 |
| Palmitoleic (cis) | 0.08 |
| 10-heptadecanoic | 0.03 |
| Gamma linolenic | 0.1 to 0.2 |
| Nonadecanoic | 0.1 to 0.2 |
| 11-transeicosenic | 0.22 |
| 11, 14 eicosandienoic | 0.1 |
| 11, 14, 17 eicosatrienoic | 0.01 |
| Eicosapentaenoic | 0.01 |
| Behenic | 0.03 |
| Erucic | 0.02 |
| Docosapentaenoic | 0.01 |
| Tricosanoic | 0.01 |
| Lignoceric | 0.02 |
| Nervonic | 0.02 |

Also present in the product are the following "actives"

Compound

Campesterol/brassicasterol

Stigmasterol

Beta-sitostero

Phosphatidylinositiol

Phosphatidylcholine

Alpha-tocopherol

Gamma-tocopherol

The intermediate is subsequently reacted to form betaines, amine oxides and quaternary compounds as follows:

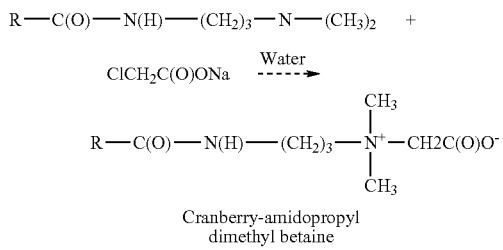

Cranberry-amidopropyl
dimethyl betaine

The current invention describes a composition, which is prepared by the reaction of:

(1) cold pressed Cranberry seed oil (2) dimethylaminopropyl amine.

The compounds of the present invention deliver these active products to skin, therefore the invention also discloses a process for conditioning skin which comprises contacting the skin with an effective conditioning concentration of a Cranberry DMAPA compound, which conforms to the following structure;

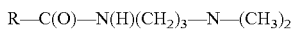

wherein;

R is derived from cold pressed Cranberry seed oil.

EXAMPLES

The compounds of the present invention are made from commercially available raw materials.

Raw Materials

Cold Pressed Cranberry Seed Oil

Cold Presses Cranberry seed oil is an item of commerce sold by Regal Trade & Consult LLC. of Hoboken, N.J. It is processed using U.S. Pat. No. 6,391,345 issued May 2002, only applied to Cranberry seed oil not cranberry seed oil.

Dimethyl Aminopropyl Amine (DMAPA)

DMAPA is an item of commerce available from several suppliers including BASF.

General Procedure

To grams of 400 grams of Cold Pressed Cranberry seed oil is added. 200 grams of dimethylaminopropyl amine.

The reaction mass is heated to 180–200° C., under good agitation. As the reaction mass is held at temperature, the material clears and becomes homogeneous. The reaction mass is held for eight hours at reaction temperature, during that time the excess DMAPA refluxed back into the batch. The reaction progress if followed by alkali value and % ester. During the reaction the Alkali Value stabilizes and does not change over a 2 hour period at temperature, and the % ester becomes vanishingly small. The excess DMAPA is stripped off. The resulting product is used without additional purification.

Preparation of the Betaine

To a suitable reaction vessel equipped with agitation and heating capabilities is added grams of the Cranberry amidopropyl dimethyl amine. Next add grams of sodium monochloroacetic acid under good agitation. The resulting mixture is heated to 80–90° C. and held 8–10 hours, keeping the pH between 8–9 by addition of small amounts of NaOH as required. During this time NaCl is generated and followed by titration. When the % NaCl reaches 98% of the theoretical, the reaction is cooled. The resulting product is a clear yellow liquid that is used without additional purification.

Applications Examples

The compound of the present invention are water-soluble surface active compound that has an extraordinary skin feel and provide antioxidant, and other desirable properties from the components that are not removed from the Cranberry oil when it is cold processed. The cold processing leaves behind the desirable components, which in turn are not destroyed by the reaction and surprisingly, become oil-soluble and delivered to the skin.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed;

1. A cranberry amido amine, which conforms to the following structure;

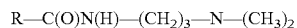

wherein;

R is derived from cold pressed cranberry seed oil, wherein the R—C(O)— group has the following composition:

| Component | % Weight |
|---|---|
| 16:0 palmitic | 5.0 to 6.0 |
| 18:0 stearic | 1.0 to 2.0 |
| 18:1 oleic | 20 to 25 |
| 18:2 linoleic | 35 to 40 |
| 18:3 linolenic (alpha) | 30 to 35 |
| 20:0 arachidic | 0.13 |
| 20:1 gadoleic | 0.20 |
| 20:5 (n-3) | 0.32 |
| 22:2 | 1.1 |
| Myristic | 0.01 |
| Pentadecanoic | 0.02 |
| Palmitoleic (trans) | 0.13 |
| Palmitoleic (cis) | 0.08 |
| 10-heptadecanoic | 0.03 |
| Gamma linolenic | 0.1 to 0.2 |
| Nonadecanoic | 0.1 to 0.2 |
| 11-transeiconsenic | 0.22 |
| 11, 14 eicosandienoic | 0.1 |
| 11, 14, 17 eicosatriencoic | 0.01 |
| Eicosapentaenoic | 0.01 |
| Behenic | 0.03 |
| Erucic | 0.02 |
| Docosapentaenoic | 0.01 |
| Tricosanoic | 0.01 |
| Lignoceric | 0.02 |
| Nervonic | 0.02. |

2. A cranberry betaine, which conforms to the following structure;

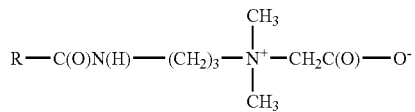

wherein;
R is derived from cold pressed Cranberry seed oil, wherein the R—C(O)— group has the following composition:

| Component | % Weight |
| --- | --- |
| 16:0 palmitic | 5.0 to 6.0 |
| 18:0 stearic | 1.0 to 2.0 |
| 18:1 oleic | 20 to 25 |
| 18:2 linoleic | 35 to 40 |
| 18:3 linolenic (alpha) | 30 to 35 |
| 20:0 arachidic | 0.13 |
| 20:1 gadoleic | 0.20 |
| 20:5 (n-3) | 0.32 |
| 22:2 | 1.1 |
| Myristic | 0.01 |
| Pentadecanoic | 0.02 |
| Palmitoleic (trans) | 0.13 |
| Palmitoleic (cis) | 0.08 |
| 10-heptadecanoic | 0.03 |
| Gamma linolenic | 0.1 to 0.2 |
| Nonadecanoic | 0.1 to 0.2 |
| 11-transeiconsenic | 0.22 |
| 11, 14 eicosandienoic | 0.1 |
| 11, 14, 17 eicosatriencoic | 0.01 |
| Eicosapentaenoic | 0.01 |
| Behenic | 0.03 |
| Erucic | 0.02 |
| Docosapentaenoic | 0.01 |
| Tricosanoic | 0.01 |
| Lignoceric | 0.02 |
| Nervonic | 0.02. |

* * * * *